United States Patent
Kumon et al.

(10) Patent No.: US 8,618,273 B2
(45) Date of Patent: Dec. 31, 2013

(54) PARTIAL FRAGMENT OF REIC/DKK-3 GENE AND CANCER THERAPEUTIC AGENT COMPRISING THE SAME

(76) Inventors: Hiromi Kumon, Okayama (JP); Nam-ho Huh, Okayama (JP); Masakiyo Sakaguchi, Okayama (JP); Yasutomo Nasu, Okayama (JP); Fernando Guillermo Abarzua Cabezas, Okayama (JP)

( * ) Notice: Subject to any disclaimer, the term of this patent is extended or adjusted under 35 U.S.C. 154(b) by 938 days.

(21) Appl. No.: 12/447,044

(22) PCT Filed: Oct. 24, 2007

(86) PCT No.: PCT/JP2007/071170
§ 371 (c)(1),
(2), (4) Date: Apr. 24, 2009

(87) PCT Pub. No.: WO2008/050898
PCT Pub. Date: May 2, 2008

(65) Prior Publication Data
US 2010/0173404 A1   Jul. 8, 2010

(30) Foreign Application Priority Data
Oct. 24, 2006   (JP) ................... 2006-289040

(51) Int. Cl.
C07H 21/02 (2006.01)
C07H 21/04 (2006.01)

(52) U.S. Cl.
USPC ........................ 536/23.5; 536/23.1

(58) Field of Classification Search
None
See application file for complete search history.

(56) References Cited

U.S. PATENT DOCUMENTS

| 7,125,957 B1 | 10/2006 | Aida et al. |
| 2006/0275263 A1 | 12/2006 | Namba et al. |
| 2009/0005538 A1 | 1/2009 | Kumon et al. |

FOREIGN PATENT DOCUMENTS

| JP | 2006-121915 | 5/2006 |
| JP | 3813872 B2 | 8/2006 |
| WO | 01/38523 A1 | 5/2001 |

OTHER PUBLICATIONS

Abarzua F et al: "An N-terminal 78 amino acid truncation of REIC/Dkk-3 effectively induces apoptosis" Biochemical and Biophysical Research Communications, Academic Press Inc. Orlando, FL, US, vol. 375, No. 4, Oct. 31, 2008, pp. 614-618.
Bernard Laurence et al: "The amino-terminal region of insulin-like growth factor binding protein-3, 1-95IGFBP-3, induces apoptosis of MCF-7 breast carcinoma cells" Biochemical and Biophysical Research Communications, vol. 293, No. 1, Apr. 26, 2002, pp. 55-60.
Tsuji T et al: "Antiproliferative Activity of REIC/Dkk-3 and Its Significant Down-Regulation in Non-Small-Cell Lung Carcinomas" Biochemical and Biophysical Research Communications, Academic Press Inc. Orlando, FL, US, vol. 289, No. 1, Jan. 1, 2001, pp. 257-263.
Tsuji T et al: "A REIC Gene Shows Down-Regulation in Human Immortalized Cells and Human Tumor-Derived Cell Lines" Jan. 1, 2000, Biochemical and Biophysical Research Communications, Academic Press Inc. Orlando, FL, US, pp. 20-24.
Hsieh et al., "Dickkopf-3/REIC functions as a suppressor gene of tumor growth," Oncogene, 2004, vol. 23, pp. 9183-9189.
Abarzua et al., "Adenovirus-mediated overexpression of REIC/Dkk-3 selectively induces apoptosis in human prostate cancer cells through activation of c-Jun-NH$_2$-Kinase," Cancer Research, Nov. 1, 2005, vol. 65, No. 21, pp. 9617-9622.

Primary Examiner — Anne-Marie Falk
(74) Attorney, Agent, or Firm — Fitch, Even, Tabin & Flannery, LLP

(57) ABSTRACT

This invention provides an inducer of apoptosis in cancer cells comprising a fragment of the REIC/Dkk-3 gene and a cancer therapeutic agent comprising the same. This invention also provides a polynucleotide fragment encoding the REIC/Dkk-3 protein (a) or (b), which encodes a polypeptide having apoptosis activity: (a) a polynucleotide encoding a polypeptide comprising an amino acid sequence of amino acid 1 to any of amino acids 39 to 78 of the amino acid sequence of the REIC/Dkk-3 protein as shown in SEQ ID NO: 2; or (b) a polynucleotide encoding a polypeptide comprising an amino acid sequence derived from the amino acid sequence of amino acid 1 to any of amino acids 39 to 78 of the amino acid sequence of the REIC/Dkk-3 protein as shown in SEQ ID NO: 2 by substitution, deletion, or addition of 1 or several amino acids and having apoptosis activity.

7 Claims, 10 Drawing Sheets
(4 of 10 Drawing Sheet(s) Filed in Color)

SEQUENCE LISTING

<160> NUMBER OF SEQ ID NOS: 8

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1050)

<400> SEQUENCE: 1

| atg | cag | cgg | ctt | ggg | gcc | acc | ctg | ctg | tgc | ctg | cta | ctg | gcg | gcg | gcg | 48 |
| Met | Gln | Arg | Leu | Gly | Ala | Thr | Leu | Leu | Cys | Leu | Leu | Leu | Ala | Ala | Ala | |
| 1 | | | | 5 | | | | | 10 | | | | | 15 | | |

| gtc | ccc | acg | gcc | ccc | gcg | ccc | gct | ccg | acg | gcg | acc | tcg | gct | cca | gtc | 96 |
| Val | Pro | Thr | Ala | Pro | Ala | Pro | Ala | Pro | Thr | Ala | Thr | Ser | Ala | Pro | Val | |
| | | | 20 | | | | | 25 | | | | | 30 | | | |

| aag | ccc | ggc | ccg | gct | ctc | agc | tac | ccg | cag | gag | gag | gcc | acc | ctc | aat | 144 |
| Lys | Pro | Gly | Pro | Ala | Leu | Ser | Tyr | Pro | Gln | Glu | Glu | Ala | Thr | Leu | Asn | |
| | | 35 | | | | | 40 | | | | | 45 | | | | |

| gag | atg | ttc | cgc | gag | gtt | gag | gaa | ctg | gtg | gag | gac | acg | cag | cac | aaa | 192 |
| Glu | Met | Phe | Arg | Glu | Val | Glu | Glu | Leu | Val | Glu | Asp | Thr | Gln | His | Lys | |
| 50 | | | | | 55 | | | | | 60 | | | | | | |

| ttg | cgc | agc | gcg | gtg | gaa | gag | atg | gag | gca | gaa | gaa | gct | gct | gct | aaa | 240 |
| Leu | Arg | Ser | Ala | Val | Glu | Glu | Met | Glu | Ala | Glu | Glu | Ala | Ala | Ala | Lys | |
| 65 | | | | | 70 | | | | | 75 | | | | | 80 | |

| gca | tca | tca | gaa | gtg | aac | ctg | gca | aac | tta | cct | ccc | agc | tat | cac | aat | 288 |
| Ala | Ser | Ser | Glu | Val | Asn | Leu | Ala | Asn | Leu | Pro | Pro | Ser | Tyr | His | Asn | |
| | | | | 85 | | | | | 90 | | | | | 95 | | |

| gag | acc | aac | aca | gac | acg | aag | gtt | gga | aat | aat | acc | atc | cat | gtg | cac | 336 |
| Glu | Thr | Asn | Thr | Asp | Thr | Lys | Val | Gly | Asn | Asn | Thr | Ile | His | Val | His | |
| | | | 100 | | | | | 105 | | | | | 110 | | | |

| cga | gaa | att | cac | aag | ata | acc | aac | aac | cag | gct | cga | caa | atg | gtc | ttt | 384 |
| Arg | Glu | Ile | His | Lys | Ile | Thr | Asn | Asn | Gln | Ala | Arg | Gln | Met | Val | Phe | |
| | | | 115 | | | | | 120 | | | | | 125 | | | |

| tca | gag | aca | gtt | atc | aca | tct | gtg | gga | gac | gaa | gaa | ggc | aga | agg | agc | 432 |
| Ser | Glu | Thr | Val | Ile | Thr | Ser | Val | Gly | Asp | Glu | Glu | Gly | Arg | Arg | Ser | |
| | | 130 | | | | | 135 | | | | | 140 | | | | |

| cac | gag | tgc | atc | atc | gac | gag | gac | tgt | ggg | ccc | agc | atg | tac | tgc | cag | 480 |
| His | Glu | Cys | Ile | Ile | Asp | Glu | Asp | Cys | Gly | Pro | Ser | Met | Tyr | Cys | Gln | |
| 145 | | | | | 150 | | | | | 155 | | | | | 160 | |

| ttt | gcc | agc | ttc | cag | tac | acc | tgc | cag | cca | tgc | cgg | ggc | cag | agg | atg | 528 |
| Phe | Ala | Ser | Phe | Gln | Tyr | Thr | Cys | Gln | Pro | Cys | Arg | Gly | Gln | Arg | Met | |
| | | | | 165 | | | | | 170 | | | | | 175 | | |

| ctc | tgc | acc | cgg | gac | agt | gag | tgc | tgt | gga | gac | cag | ctg | tgt | gtc | tgg | 576 |
| Leu | Cys | Thr | Arg | Asp | Ser | Glu | Cys | Cys | Gly | Asp | Gln | Leu | Cys | Val | Trp | |
| | | | 180 | | | | | 185 | | | | | 190 | | | |

| ggt | cac | tgc | acc | aaa | atg | gcc | acc | agg | ggc | agc | aat | ggg | acc | atc | tgt | 624 |
| Gly | His | Cys | Thr | Lys | Met | Ala | Thr | Arg | Gly | Ser | Asn | Gly | Thr | Ile | Cys | |
| | | | 195 | | | | | 200 | | | | | 205 | | | |

| gac | aac | cag | agg | gac | tgc | cag | ccg | ggg | ctg | tgc | tgt | gcc | ttc | cag | aga | 672 |
| Asp | Asn | Gln | Arg | Asp | Cys | Gln | Pro | Gly | Leu | Cys | Cys | Ala | Phe | Gln | Arg | |
| | | 210 | | | | | 215 | | | | | 220 | | | | |

| ggc | ctg | ctg | ttc | cct | gtg | tgc | ata | ccc | ctg | ccc | gtg | gag | ggc | gag | ctt | 720 |
| Gly | Leu | Leu | Phe | Pro | Val | Cys | Ile | Pro | Leu | Pro | Val | Glu | Gly | Glu | Leu | |
| 225 | | | | | 230 | | | | | 235 | | | | | 240 | |

| tgc | cat | gac | ccc | gcc | agc | cgg | ctt | ctg | gac | ctc | atc | acc | tgg | gag | cta | 768 |
| Cys | His | Asp | Pro | Ala | Ser | Arg | Leu | Leu | Asp | Leu | Ile | Thr | Trp | Glu | Leu | |
| | | | | 245 | | | | | 250 | | | | | 255 | | |

| gag | cct | gat | gga | gcc | ttg | gac | cga | tgc | cct | tgt | gcc | agt | ggc | ctc | ctc | 816 |

```
Glu Pro Asp Gly Ala Leu Asp Arg Cys Pro Cys Ala Ser Gly Leu Leu
            260                 265                 270 tgc cag ccc cac agc cac agc ctg gtg tat gtg tgc aag ccg acc ttc      864
Cys Gln Pro His Ser His Ser Leu Val Tyr Val Cys Lys Pro Thr Phe
        275                 280                 285 gtg ggg agc cgt gac caa gat ggg gag atc ctg ctg ccc aga gag gtc      912
Val Gly Ser Arg Asp Gln Asp Gly Glu Ile Leu Leu Pro Arg Glu Val
        290                 295                 300 ccc gat gag tat gaa gtt ggc agc ttc atg gag gag gtg cgc cag gag      960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag     1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag         1053
Pro Ala Ala Ala Ala Ala Leu Leu Gly Gly Glu Glu Ile
                340                 345                 350

<210> SEQ ID NO 2
<211> LENGTH: 350
<212> TYPE: PRT
<213> ORGANISM: Homo sapiens

<400> SEQUENCE: 2

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Val Glu Asp Thr Gln His Lys
    50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Ala Arg Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205

Asp Asn Gln Arg Asp Cys Gln Pro Gly Leu Cys Cys Ala Phe Gln Arg
    210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
```

```
                     260                 265                 270
Cys Gln Pro His Ser His Ser Leu Val Tyr Val Cys Lys Pro Thr Phe
            275                 280                 285

Val Gly Ser Arg Asp Gln Asp Gly Glu Ile Leu Leu Pro Arg Glu Val
        290                 295                 300

Pro Asp Glu Tyr Glu Val Gly Ser Phe Met Glu Val Arg Gln Glu
305                 310                 315                 320

Leu Glu Asp Leu Glu Arg Ser Leu Thr Glu Met Ala Leu Gly Glu
                325                 330                 335

Pro Ala Ala Ala Ala Ala Leu Leu Gly Gly Glu Glu Ile
            340                 345                 350

<210> SEQ ID NO 3
<211> LENGTH: 117
<212> TYPE: DNA
<213> ORGANISM: Homo sapiens

<400> SEQUENCE: 3
atgcagcggc ttggggccac cctgctgtgc ctgctactgg cggcggcggt ccccacggcc    60
cccgcgcccg ctccgacggc gacctcggct ccagtcaagc ccggcccggc tctcagc     117

<210> SEQ ID NO 4
<211> LENGTH: 39
<212> TYPE: PRT
<213> ORGANISM: Homo sapiens

<400> SEQUENCE: 4

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser
        35

<210> SEQ ID NO 5
<211> LENGTH: 234
<212> TYPE: DNA
<213> ORGANISM: Homo sapiens

<400> SEQUENCE: 5
atgcagcggc ttggggccac cctgctgtgc ctgctactgg cggcggcggt ccccacggcc    60
cccgcgcccg ctccgacggc gacctcggct ccagtcaagc ccggcccggc tctcagctac   120
ccgcaggagg aggccaccct caatgagatg ttccgcgagg ttgaggaact ggtggaggac   180
acgcagcaca aattgcgcag cgcggtggaa gagatggagg cagaagaagc tgct         234

<210> SEQ ID NO 6
<211> LENGTH: 78
<212> TYPE: PRT
<213> ORGANISM: Homo sapiens

<400> SEQUENCE: 6

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Val Glu Asp Thr Gln His Lys
```

```
                50                  55                  60
Leu Arg Ser Ala Val Glu Glu Met Glu Ala Glu Ala Ala
 65                  70                  75

<210> SEQ ID NO 7
<211> LENGTH: 57
<212> TYPE: DNA
<213> ORGANISM: Homo sapiens

<400> SEQUENCE: 7
atgcagcggc ttggggccac cctgctgtgc ctgctactgg cggcggcggt ccccacg       57

<210> SEQ ID NO 8
<211> LENGTH: 19
<212> TYPE: PRT
<213> ORGANISM: Homo sapiens

<400> SEQUENCE: 8

Met Gln Arg Leu Gly Ala Thr Leu Leu Cys Leu Leu Leu Ala Ala Ala
 1               5                  10                  15

Val Pro Thr
```

PARTIAL FRAGMENT OF REIC/DKK-3 GENE AND CANCER THERAPEUTIC AGENT COMPRISING THE SAME

CROSS-REFERENCE TO RELATED APPLICATIONS

This is a U.S. National Phase of International Application PCT/JP2007/071170, filed Oct. 24, 2007, and claims foreign priority under 35 U.S.C. §119 based on Japanese Application No. 2006-289040, filed Oct. 24, 2006, the entire disclosures of which applications, including any and all sequence listings, are hereby incorporated herein by reference.

TECHNICAL FIELD

The present invention relates to induction of apoptosis in cancer cells using a tumor suppressor gene; i.e., a fragment of the REIC/Dkk-3 gene, an inducer of apoptosis in cancer cells comprising a fragment of the REIC/Dkk-3 gene, and a cancer therapeutic agent comprising the inducer of apoptosis.

BACKGROUND ART

Selective removal of cancer cells plays a key role in treatment of cancer. Various types of genetic mutations occur in cells during the processes of oncogenesis and cancer progression (Vogelstein, B. et al., Trends Genet 9, 138-41, 1993), and such mutations can be the targets of cancer gene therapy. When genes of a given type are overexpressed, such genes exhibit the effects of selectively killing cancer cells. Representative examples of such genes include p53 (Chen, P. L. et al., Science 250, 1576-80, 1990; Fujiwara, T. et al., J. Natl. Cancer Inst., 86, 1458-62, 1994; Nielsen, L. L. et al., Cancer Gene Ther., 4, 129-38, 1997) and mda-7 (Fisher, P. B. et al., Cancer Biol. Ther., 2, S23-37, 2003), and such genes are known as cancer suppressor genes.

Meanwhile, the REIC/Dkk-3 gene is known to be associated with cell immortalization, and suppression of expression of such genes in cancer cells has been reported (WO 01/038523, Tsuji, T. et at, Biochem. Biophys. Res. Commun., 268, 20-4, 2000; Tsuji, T. et al., Biochem. Biophys. Res. Commun., 289, 257-63, 2001; Nozaki, I. et al., Int. J. Oncol., 19, 117-21, 2001; and Kurose, K. et al., J. Urol., 171, 1314-8, 2004).

The REIC/Dkk-3 gene is a member of the Dkk family, and it is suggested that such gene inhibits Wnt signal transmission via a Wnt receptor (Bafico, A. et al., Nat. Cell Biol., 3, 683-6, 2001 and Hoang, B. H. et al., Cancer Res., 64, 2734-9, 2004). It is reported that the Wnt gene plays multiple roles in important biological conditions, such as cell growth, differentiation, and canceration (Moon, R. T. et al., Science 296, 1644-6, 2002). Accordingly, the Dkk family (the presence of 4 genes is known in humans at present) is also considered to play a key role in cell growth, differentiation, and canceration, although most of its functions remain unknown.

At present, research regarding endoplasmic reticulum stress has been in progress. Secretory proteins synthesized in vivo is transferred to the endoplasmic reticulum and efficiently folded by a variety of molecular chaperones or folding enzymes. However, folding cannot always be sufficiently performed, abnormal proteins of a higher-order structure are accumulated in the endoplasmic reticulum in such a case, and endoplasmic reticulum stress is induced thereby (D. Thomas Rutkowski et al., TRENDS in Cell Biology Vol. 14, No. 1, p. 20-28, January 2004). It is reported that cells may die because of apoptosis induced by the endoplasmic reticulum stress (Mori K., Traffic, 4, 519-528, 2003).

DISCLOSURE OF THE INVENTION

The present invention provides an inducer of apoptosis in cancer cells comprising a fragment of the REIC/Dkk-3 gene and a cancer therapeutic agent comprising the inducer of apoptosis.

Up to the present, the present inventors have demonstrated that forced expression of REIC/Dkk-3 by adenovirus would induce apoptosis in cancer cells, such as prostate cancer cells, normal cells would not be significantly influenced under the same conditions, and significant effects of treating cancer would be observed in animal transplant models (JP Patent No. 3813872 and WO 2006/098074). Further, the present inventors have conducted concentrated studies regarding the region of the REIC/Dkk-3 protein that would exhibit the strongest effects of induction of apoptosis and the mechanism of exhibiting the effects of induction of apoptosis.

Consequently, the present inventors discovered the following.

(1) Apoptosis is not observed when the REIC/Dkk-3 gene is introduced into the CHO cell to forcibly express REIC/Dkk-3, and the REIC/Dkk-3 protein secreted in the medium is administered to the cancer cells.

(2) JNK is activated and induction of apoptosis is suppressed by the JNK inhibitor at the time of apoptosis in cancer cells via forced expression of the REIC/Dkk-3 gene. JNK is activated via various factors, and endoplasmic reticulum stress is known to be a significant factor.

(3) The CHOP and BIP genes, which are induced by stress resulting from accumulation of abnormal proteins in the endoplasmic reticulum, were induced along with forced expression of the REIC/Dkk-3 gene.

(4) Apoptosis in cancer cells did not occur when an Hsp protein inducer that would promote construction of a protein normal conformation was allowed to act on the cancer cells. In contrast, apoptosis was induced in normal cells in which apoptosis would not normally occur via forced expression of the REIC/Dkk-3 gene, when an Hsp protein inhibitor was allowed to act thereon.

(5) Apoptosis in cancer cells was induced via forced expression of a partial peptide that does not have functions inherent to REIC/Dkk-3.

Based on such findings, the present inventors discovered the possibility of involvement of endoplasmic reticulum stress as a mechanism of REIC/Dkk-3 for inducing apoptosis in cancer cells.

Further, the present inventors discovered that a fragment of the REIC/Dkk-3 gene expressed in cancer cells would induce apoptosis and would lead cancer cells to die. This has led to the completion of the present invention.

Specifically, the present invention relates to a fragment of the REIC/Dkk-3 gene. Also, the present invention relates to a fragment of the REIC/Dkk-3 gene that would cause endoplasmic reticulum stress in a cell into which the fragment has been introduced. Further, the present invention relates to a fragment of the REIC/Dkk-3 gene that would induce apoptosis in a cell into which the fragment has been introduced.

The present invention relates to a vector that can express a fragment of the REIC/Dkk-3 gene in a cell containing the above fragment.

Further, the present invention relates to an inducer of apoptosis comprising the above fragment or a vector containing such fragment. Apoptosis induced by such fragment or vector is induced via endoplasmic reticulum stress.

Further, the present invention relates to a cancer therapeutic agent comprising the above fragment or a vector containing such fragment.

Further, the present invention relates to a fragment of the REIC/Dkk-3 protein, which is a partial peptide that would cause endoplasmic reticulum stress in a cell to which such fragment is administered. Further, the present invention relates to a fragment of the REIC/Dkk-3 protein, which is a polypeptide fragment that would cause apoptosis in a cell to which such fragment is administered.

Further, the present invention relates to an inducer of apoptosis comprising the polypeptide fragment. Apoptosis induced by such polypeptide fragment is induced via endoplasmic reticulum stress.

Further, the present invention relates to a cancer therapeutic agent comprising a vector containing the above polypeptide fragment.

This description includes part or all of the contents as disclosed in the description and/or drawings of Japanese Patent Application No. 2006-289040, which is a priority document of the present application.

BRIEF DESCRIPTION OF DRAWINGS

The patent or application file contains at least one drawing executed in color. Copies of this patent or patent application publication with color drawings will be provided by the Office upon request and payment of the necessary fee.

BEST MODES FOR CARRYING OUT THE INVENTION

Figure 1:
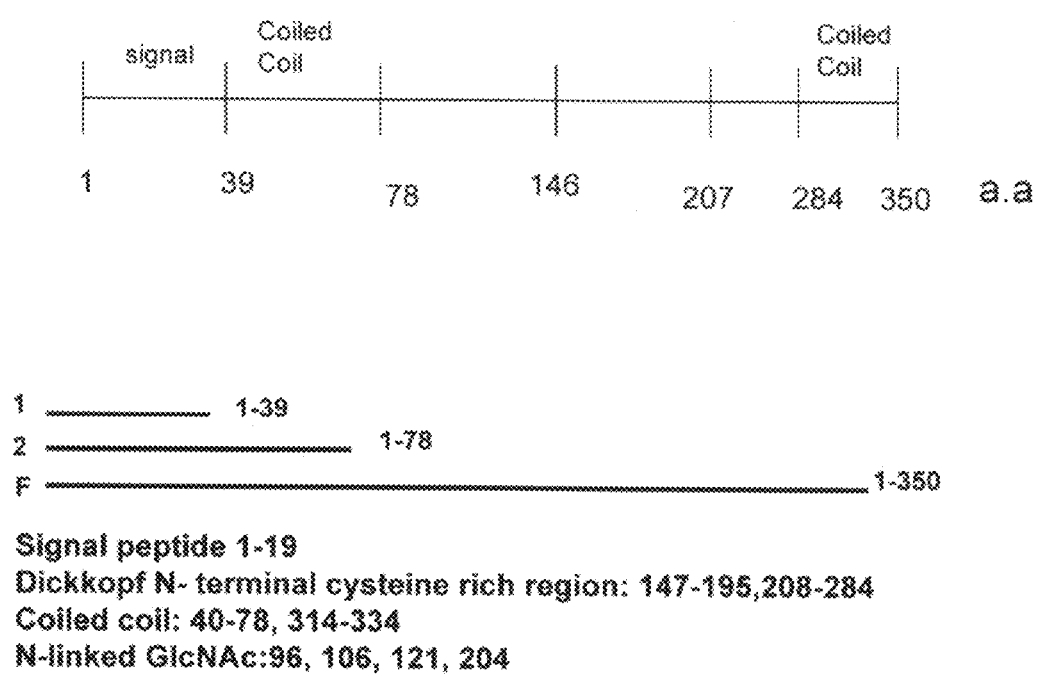
FIG. 1 shows a fragment of REIC/Dkk-3.

Hereafter, the present invention is described in detail.

The inducer of apoptosis or cancer therapeutic agent of the present invention comprises, as an active ingredient, the REIC/Dkk-3 gene fragment that induces apoptosis and has effects as a cancer therapeutic agent.

The full-length nucleotide sequence of the REIC/Dkk-3 gene and the amino acid sequence of a protein encoded by such gene are shown in SEQ ID NO: 1 and SEQ ID NO: 2, respectively. In the amino acid sequence as shown in SEQ ID NO: 2, a sequence comprising amino acids 1 to 19 is deduced to be a signal sequence. The nucleotide sequence of the signal sequence is shown in SEQ ID NO: 7 and the amino acid sequence thereof is shown in SEQ ID NO: 8. The REIC/Dkk-3 gene can be obtained from a human cell, tissue, or the like based on the sequence information of SEQ ID NO: 1. Also, such gene can be obtained in accordance with the description of WO 01/038523.

The REIC/Dkk-3 gene fragment of the present invention that induces apoptosis and has the effects as a cancer therapeutic agent comprises any of polynucleotides (a) to (p), which encodes a polypeptide having apoptosis activity:

(a) a polynucleotide encoding a polypeptide consisting of an amino acid sequence of amino acid 1 to any of amino acids 39 to 78 of the amino acid sequence of the REIC/Dkk-3 protein as shown in SEQ ID NO: 2;

(b) a polynucleotide encoding a polypeptide consisting of an amino acid sequence derived from the amino acid sequence of amino acid 1 to any of amino acids 39 to 78 of the amino acid sequence of the REIC/Dkk-3 protein as shown in SEQ ID NO: 2 by substitution, deletion, or addition of 1 or several amino acids and having apoptosis activity;

(c) a polynucleotide consisting of a nucleotide sequence of nucleotide 1 to any of nucleotides 117 to 234 of the nucleotide sequence of the REIC/Dkk-3 gene as shown in SEQ ID NO: 1;

(d) a polynucleotide hybridizing under stringent conditions to the polynucleotide consisting of a nucleotide sequence complementary to the nucleotide sequence consisting of nucleotide 1 to any of nucleotides 117 to 234 of nucleotide sequence of the REIC/Dkk-3 gene as shown in SEQ ID NO: 1 and encoding a polypeptide having apoptosis activity;

(e) a polynucleotide consisting of a nucleotide sequence encoding the amino acid sequence as shown in SEQ ID NO: 4;

(f) a polynucleotide encoding a polypeptide consisting of an amino acid sequence derived from the amino acid sequence as shown in SEQ ID NO: 4 by substitution, deletion, or addition of 1 or several amino acids and having apoptosis activity;

(g) a polynucleotide consisting of the nucleotide sequence as shown in SEQ ID NO: 3;

(h) a polynucleotide hybridizing under stringent conditions to the polynucleotide consisting of a nucleotide sequence complementary to the nucleotide sequence as shown in SEQ ID NO: 3 and encoding a polypeptide having apoptosis activity;

(i) a polynucleotide consisting of the nucleotide sequence encoding the amino acid sequence as shown in SEQ ID NO: 6;

(j) a polynucleotide encoding a polypeptide consisting of an amino acid sequence derived from the amino acid sequence as shown in SEQ ID NO: 6 by substitution, deletion, or addition of 1 or several amino acids and having apoptosis activity;

(k) a polynucleotide consisting of the nucleotide sequence as shown in SEQ ID NO: 5;

(l) a polynucleotide hybridizing under stringent conditions to the polynucleotide consisting of a nucleotide sequence complementary to the nucleotide sequence as shown in SEQ ID NO: 5 and encoding a polypeptide having apoptosis activity;

(m) a polynucleotide comprising the nucleotide sequence encoding the amino acid sequence of a polypeptide fragment comprising a signal peptide consisting of a sequence of amino acids 1 to 19 of the amino acid sequence of the REIC/Dkk-3 protein as shown in SEQ ID NO: 2, which comprises at least 39 amino acids but does not comprise the full-length sequence of the REIC/Dkk-3 protein;

(n) a polynucleotide encoding a polypeptide comprising a signal peptide consisting of a sequence of amino acids 1 to 19 of the amino acid sequence of the REIC/Dkk-3 protein as shown in SEQ ID NO: 2, which comprises an amino acid sequence derived from the amino acid sequence of a polypeptide fragment comprising at least 39 amino acid residues but does not comprise the full-length sequence of the REIC/Dkk-3 protein by substitution, deletion, or addition of 1 or several amino acids, and having apoptosis activity;

(o) a polynucleotide comprising a nucleotide sequence including a nucleotide sequence encoding a signal sequence consisting of a sequence of nucleotides 1 to 57 of the nucleotide sequence of the REIC/Dkk-3 gene as shown in SEQ ID NO: 1, which comprises at least 117 nucleotides but does not comprise the full-length nucleotide sequence of REIC/Dkk-3; or (p) a polynucleotide hybridizing under stringent conditions to the polynucleotide comprising a nucleotide sequence complementary to the nucleotide sequence including a nucleotide sequence encoding a signal sequence consisting of a sequence of nucleotides 1 to 57 of the nucleotide sequence of the REIC/Dkk-3 gene as shown in SEQ ID NO: 1, which comprises at least 117 nucleotides but lacks the full-length nucleotide sequence of REIC/Dkk-3, and encoding a polypeptide having apoptosis activity.

In (a) and (b) above, the term "an amino acid sequence of amino acid 1 to any of amino acids 39 to 78 of the amino acid sequence of the REIC/Dkk-3 protein as shown in SEQ ID NO: 2" refers to an amino acid sequence whose N terminus is amino acid 1 of the amino acid sequence as shown in SEQ ID NO: 2, whose C terminus is any of amino acids 39 to 78 of the amino acid sequence as shown in SEQ ID NO: 2, and for which the number of amino acid residues is between 39 to 78. Such amino acid sequence includes an amino acid sequence comprising amino acids 1 to any of 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, or 78 of the amino acid sequence as shown in SEQ ID NO: 2.

In (c) and (d) above, the term "a nucleotide sequence of nucleotide 1 to any of nucleotides 117 to 234 of the nucleotide sequence of the REIC/Dkk-3 gene as shown in SEQ ID NO: 1" refers to a nucleotide sequence whose 5' terminus is nucleotide 1 of the nucleotide sequence as shown in SEQ ID NO: 1 and whose 3' terminus is any of nucleotides 117 to 234 of the nucleotide sequence as shown in SEQ ID NO: 1. The number of nucleotides is between 117 to 234, and such number preferably corresponds to an amino acid sequence comprising amino acids 1 to 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, or 78 of the amino acid sequence as shown in SEQ ID NO: 2.

In (b), (f), (j), and (n) above, the term "1 or several" in the term " . . . amino acid sequence by substitution, deletion, or addition of 1 or several amino acids" refers to 1 to 10, preferably 1 to 5, and further preferably 1 or 2.

The REIC/Dkk-3 gene fragment of the present invention that induces apoptosis and has the effects of a cancer therapeutic agent includes a polynucleotide that encodes an amino acid sequence having at least 85%, preferably 90% or higher, further preferably 95% or higher, and particularly preferably 97% or higher homology to the amino acid sequence (a), (e), (i), or (m), calculated using, for example, BLAST (Basic Local Alignment Search Tool) at the National Center for Biological Information (with the use of, for example, default i.e., initial parameters).

Under "stringent conditions" in (d), (h), (l), and (p), for example, hybridization is carried out with 1×SSC, 0.1% SDS, and 37° C. Under more stringent conditions, it is carried out with 0.5×SSC, 0.1% SDS, and 42° C. Under further stringent conditions, it is carried out with 0.2×SSC, 0.1% SDS, and 65° C. Under more stringent hybridization conditions, accordingly, isolation of DNA having higher homology to a probe sequence can be expected. It should be noted that the above combinations of SSC, SDS, and temperature conditions are examples, and necessary stringency can be realized by adequately combining a probe concentration, a probe length, a hybridization reaction time, and other conditions.

The REIC/Dkk-3 gene fragment of the present invention that induces apoptosis and has the effects as a cancer therapeutic agent includes a polynucleotide, which is DNA having at least 85%, preferably 90% or higher, further preferably 95% or higher, and particularly preferably 97% or higher homology to the nucleotide sequence of the polynucleotide (c), (g), (k), or (o), when calculated using, for example, BLAST (Basic Local Alignment Search Tool) at the National Center for Biological Information (with the use of, for example, default i.e., initial parameters) and having activity of inducing apoptosis.

The aforementioned (m) and (n) include the REIC/Dkk-3 protein fragment comprising a signal peptide. The number of amino acid residues in the term "amino acid sequence of a polypeptide fragment comprising a signal peptide consisting of a sequence of amino acids 1 to 19 of the amino acid sequence of the REIC/Dkk-3 protein as shown in SEQ ID NO: 2, which comprises at least 39 amino acids but does not comprise the full-length sequence of the REIC/Dkk-3 protein" is, for example, 39, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 300, 305, 310, 315, 320, 325, 330, 335, or 340.

(o) and (p) above are each the REIC/Dkk-3 gene fragment comprising a nucleotide region encoding a signal peptide.

These fragments express polypeptides in cells, such polypeptides are transferred to the endoplasmic reticulum, but such polypeptides cannot constitute normal higher-order structures. This is considered to cause endoplasmic reticulum stress. The REIC/Dkk-3 gene fragment of the present invention preferably comprises a nucleotide sequence encoding a signal peptide in order for the expression product to be transferred to the endoplasmic reticulum.

Further, the present invention includes a vector comprising the REIC/Dkk-3 gene fragment. The vector may be introduced into a subject to express a polypeptide encoded by the REIC/Dkk-3 gene fragment in the body of the subject and exhibit the effects of apoptosis induction. In genetic therapy, the target gene can be introduced into the subject in accordance with a conventional technique. Examples of techniques for introducing a gene into a subject include a method involving the use of a virus vector and a method involving the use of a non-virus vector. Various techniques are known (Bessatsu Jikken-Igaku, Idenshi-Chiryo-No-Kisogijutsu (*Basic Techniques for Gene Therapy*), Yodosha Co., Ltd., 1996; Bessatsu Jikken Igaku (*Separate volume, Experimental Medicine*), Idenshi donyu & hatsugen kaiseki jikken-hou (*Experimentation of gene introduction & expression analysis*), Yodosha, Co., Ltd.; and the Japan Society of Gene Therapy (ed.), "*Idenshi chiryo kaihatsu kenkyu handbook* (*the Handbook for research and development of gene therapy*)," N.T.S., 1999).

Representative examples of virus vectors used for gene introduction include an adenovirus vector, an adeno-associated virus vector, and a retrovirus vector. A target gene may be introduced into a cell by introducing a target gene into a DNA or RNA virus, such as a detoxicated retrovirus, herpes virus, vaccinia virus, poxvirus, poliovirus, Sindbis virus, Sendai virus, SV40, or HIV, and infecting the cell with such virus.

When the gene of the present invention is used for genetic therapy using a virus, an adenovirus vector is preferably used. An adenovirus vector is characterized in that: (1) it can introduce genes into multiple types of cells; (2) it can efficiently introduce genes into cells at the period of growth arrest; (3) it enables concentration via centrifugation to yield high-titer viruses (10 to 11 PFU/ml or more); and (4) it is suitable for direct gene introduction into tissue or cells in vivo. As adenovirus vectors used for genetic therapy, a first-generation adenovirus vector lacking the E1/E3 region (Miyake, S. et al., Proc. Natl. Acad. Sci., U.S.A., 93, 1320, 1996), the second-generation adenovirus vector prepared from the first-generation adenovirus vector by deleting the E2 or E4 region in addition to the E1/E3 region (Lieber, A. et al., J. Virol., 70, 8944, 1996; Mizuguchi, H. & Kay, M. A., Hum. Gene Ther., 10, 2013, 1999), and the third-generation adenovirus vector lacking substantially all the adenovirus genome (GUTLESS) (Steinwaerder, D. S., et al., J. Virol., 73, 9303, 1999) have been developed. The gene of the present invention can be introduced with the use of any of such adenovirus vectors without particular limitation. Further, the adeno-AAV hybrid vector to which the capacity for incorporating the gene into the AAV chromosome has been imparted (Recchia, A. et al., Proc. Natl. Acad. Sci., U.S.A., 96, 2615, 1999) or an adenovirus vector capable of incorporating the gene into the chromosome with the use of a transposon gene may be used, so that such vector can be applied to long-term gene expression. Also, a peptide sequence exhibiting tissue-specific transferability to the Hi loop of the adenovirus fiber may be inserted to impart tissue specificity to the adenovirus vector (Mizuguchi, H. & Hayakawa, T., Nippon Rinsho, 7, 1544, 2000).

Alternatively, the target gene can be introduced into a cell or tissue using a recombinant expression vector into which a gene expression vector, such as a plasmid vector, has been incorporated, without the use of the above viruses. For example, a gene can be introduced into a cell via lipofection, calcium phosphate coprecipitation, a DEAE-dextran method, or direct injection of DNA using a micro glass tube. Also, a recombinant expression vector can be incorporated into a cell via, for example, gene introduction using an internal liposome, gene introduction using an electorostatic type liposome, a method using HVJ-liposome, a method using a modified HVJ-liposome (i.e., the HVJ-AVE liposome method), a method using an HVJ-E (envelope) vector, receptor-mediated gene introduction, a method in which a particle gun is used to introduce DNA molecules in a cell with a carrier (i.e., a metal particle), direct introduction of naked-DNA, or gene introduction using various types of polymers. In such a case, any expression vector can be used, provided that such vector can express the target gene in vivo. Examples of such vectors include pCAGGS (Gene 108, 193-200, 1991), pBK-CMV, pcDNA3, 1, and pZeoSV (Invitrogen, Stratagene), and pVAX1 vectors.

A vector comprising the REIC/Dkk-3 gene fragment may adequately comprise a promoter or enhancer for transcribing the gene, poly A signal, a marker gene for labeling and/or selecting the cell into which the gene has been introduced, and the like. In such a case, a known promoter can be used.

A pharmaceutical composition comprising the REIC/Dkk-3 gene fragment of the present invention may be introduced into a subject by, for example; the in vivo method wherein a gene therapeutic agent is directly introduced into the body or the ex vivo method wherein a given cell is extracted from a human, a gene therapeutic agent is introduced into the cell ex vivo, and the cell is then returned into the body (Nikkei Science, April 1994, pp. 20-45; Gekkan Yakuji, 36(1), 23-48, 1994; Jikken igaku zoukan, 12(15), 1994; the Japan Society of Gene Therapy (ed.), Idenshi chiryo kaihatsu kenkyu handbook, N. T. S., 1999).

Further, the inducer of apoptosis or cancer therapeutic agent of the present invention comprises, as an active ingredient, a polypeptide fragment of the REIC/Dkk-3 protein that induces apoptosis and has the effects as a cancer therapeutic agent.

Such polypeptide fragment includes a polypeptide fragment of the REIC/Dkk-3 protein according to (a), (b), (e), (f), (i), or (j), which has apoptosis activity:

(a) a polypeptide consisting of an amino acid sequence of amino acid 1 to any of amino acids 39 to 78 of the amino acid sequence of the REIC/Dkk-3 protein as shown in SEQ ID NO: 2;

(b) a polypeptide consisting of an amino acid sequence derived from the amino acid sequence of amino acid 1 to any of amino acids 39 to 78 of the amino acid sequence of the REIC/Dkk-3 protein as shown in SEQ ID NO: 2 by substitution, deletion, or addition of 1 or several amino acids and having apoptosis activity;

(e) a polypeptide consisting of the amino acid sequence as shown in SEQ ID NO: 4;

(f) a polypeptide consisting of an amino acid sequence derived from the amino acid sequence as shown in SEQ ID NO: 4 by substitution, deletion, or addition of 1 or several amino acids and having apoptosis activity;

(i) a polypeptide consisting of the amino acid sequence as shown in SEQ ID NO: 6; and (j) a polypeptide consisting of an amino acid sequence derived from the amino acid sequence as shown in SEQ ID NO: 6 by substitution, deletion, or addition of 1 or several amino acids and having apoptosis activity.

Details of the polypeptide fragments of the REIC/Dkk-3 protein (a), (b), (e), (f), (i), and (j) are as described above.

The protein of the present invention encoded by the gene of the present invention induces the aging or resting state of a receptor cell and thus can mediate cancer cells to differentiate into noncancerous cells. For example, such protein can be used for treatment for suppressing acute growth of cancer or primordial cancer cells.

In general, tumors are classified into benign tumors and malignant tumors, and the latter tumors are collectively referred to as "cancer."

Tumors that can be treated with the use of the protein of the present invention are not particularly limited, benign and malignant tumors can be treated, and the protein of the present invention is particularly effective on malignant tumors.

Malignant tumors are classified into cranial nerve tumor, skin cancer, gastric cancer, lung cancer, hepatic cancer, lymphoma/leukemia, colon cancer, pancreatic cancer, anal/rectal cancer, esophageal cancer, uterine cancer, breast cancer, osteoma/osteosarcoma, leiomyoma, rhabdomyoma, mesoepithelioma, and other cancers in accordance with organs the locations at which the tumors develop. As described above, tumors that can be treated are not particularly limited, and the above tumors and cancers can be treated. The protein of the present invention is particularly effective on prostate cancer, lung cancer, hepatic cancer, gastric cancer, esophageal cancer, head and neck cancer, ovarian cancer, and osteoma/osteosarcoma. The protein is further effective on prostate cancer and mesoepithelioma, and particularly effective on highly malignant prostate cancer. The term "highly malignant prostate cancer" used herein refers to prostate cancer having a Gleason score of 8 or higher, for example.

Further, cancers developed in such organs are roughly classified into epithelial cell-derived carcinoma, non-epithelial cell-derived sarcoma, and mixed tumors thereof in terms of histological properties. Tumors that can be treated with the use of the protein of the present invention are not particularly limited, and epithelial cell-derived carcinoma, non-epithelial cell-derived sarcoma, and mixed tumor thereof can be treated. The protein of the present invention is particularly effective on epithelial cell-derived carcinoma.

The pharmaceutical composition of the present invention comprises the REIC/Dkk-3 gene fragment or a vector comprising the same and a pharmacologically acceptable carrier, diluent, or excipient.

Further, the pharmaceutical composition of the present invention comprises the REIC/Dkk-3 polypeptide fragment and a pharmacologically acceptable carrier, diluent, or excipient.

The pharmaceutical composition of the present invention can be administered in a variety of dosage forms. Examples of dosage forms include: oral administration, such as a tablet, capsule, granule, powder, and syrup; and parenteral administration, such as injection, drop, suppository, spray, eye drop, nasal agent, and patch.

The pharmaceutical composition of the present invention can be topically administered. For example, the composition can be administered to a site of cancer via injection to provide the effects thereof.

The pharmaceutical composition of the present invention comprises a carrier, a diluent, and an excipient that are generally used in the drug manufacturing field. For example, lactose or magnesium stearate can be used as a carrier or excipient of a tablet. An isotonic solution containing physiological saline, glucose, and another adjuvant is used as an aqueous solution of an injection. An isotonic solution may be used in combination with an adequate solubilizer, such as alcohol, a polyalcohol such as propylene glycol, or a nonionic surfactant. Sesame oil, soybean oil, or the like is used as an oily liquid, and, as a solubilizer, benzyl benzoate, benzyl alcohol, or the like may be used in combination.

The dose varies depending on symptoms, age, body weight, and other conditions. In the case of the REIC/Dkk-3 gene fragment or a vector comprising the same, a dose may be 0.001 mg to 100 mg of the REIC/Dkk-3 polynucleotide fragment at intervals of several days, several weeks, or several months, and such polynucleotide fragment may be administered via hypodermic injection, intramuscular injection, or intravenous injection. In the case of the REIC/Dkk-3 polypeptide fragment, a dose in the case of oral administration may be between about 0.001 mg and 100 mg per day, and such fragment may be administered once or several separate doses. In the case of parenteral administration, a dose of 0.001 mg to 100 mg may be administered via hypodermic injection, intramuscular injection, or intravenous injection.

The present invention is hereafter described in detail with reference to the following examples, although the technical scope of the present invention is not limited thereto.

Example 1

Induction of Apoptosis by REIC/Dkk-3 Gene Fragment (1)

This example was performed using the materials below in the following manner.

(1) Cell Culture:

The human prostate cancer-derived cell lines (PC3) were cultured using the HAM'S F-12 K medium to which 10% fetal bovine serum had been added.

(2) Preparation of Recombinant Plasmid:

Full-length cDNA of REIC/Dkk-3 (F: 1-350 aa) and fragments thereof (1: 1-39 aa; 2: 1-78 aa) were prepared via PCR using synthetic primers, and the resultants were digested with EcoR1 and XhoI restriction enzymes and then incorporated into plasmids (pDNR-CMV) (pDNR-CMV-F, -1, and -2). FIG. 1 shows positions of the fragments on the REIC/Dkk-3 protein.

(3) Introduction of Recombinant Plasmid into Cell:

The plasmids prepared above were introduced into the PC3 cells via magnetofection (plasmids, a transfection reagent (DreamFect reagent; OZ BIOSCIENCES, Marseille France), and magnetic nanoparticles were mixed, the resultant was added to the cell culture system, and the cells were allowed to stand on a magnet plate for 30 minutes). The efficiency for introducing plasmids into cells was evaluated using the GFP expression plasmid (pDNR-CMV-GFP) and the efficiency was found to be as high as approximately 70% 24 hours after introduction.

(4) Evaluation of Cell Death:

Cell death was evaluated 72 hours after the introduction of the plasmids. Evaluation was carried out by a staining method involving the use of ethidium homodimer 1 (stain for dead cells: red fluorescent) in combination with Hoechst 33342 (stain for all cells: blue fluorescent). In this system, the number of dead cells (i.e., ethidium homodimer-1-positive cells) among 100 cells (i.e., Hoechst 33342-positive cells) was counted four times in total, and the percentage of dead cells was determined.

Figure 2:
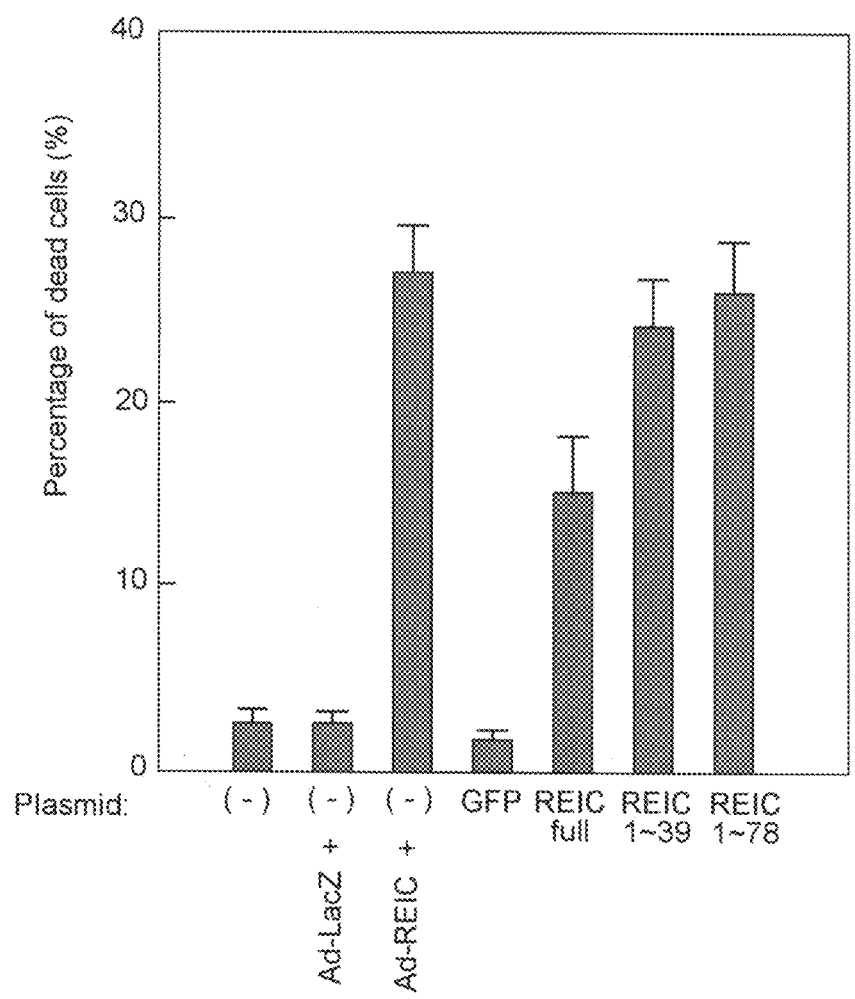
FIG. 2 shows activity of the REIC/Dkk-3 gene fragments for inducing cell death.
Figure 3:
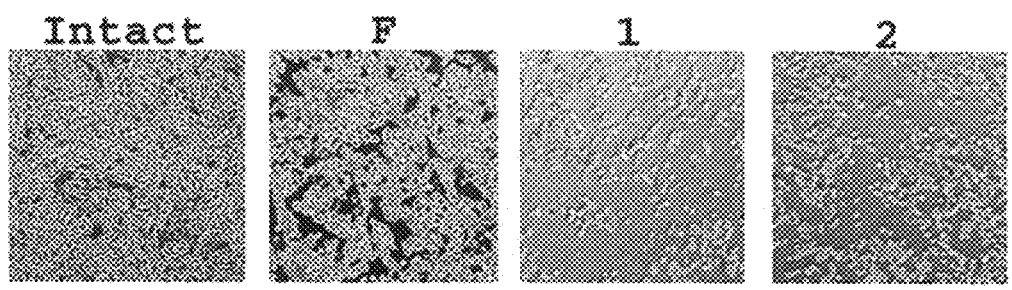
FIG. 3 is a photograph showing the conditions of PC3 cell death induced by the REIC/Dkk-3 gene fragments (part I).

FIG. 2 shows the percentage of dead cells when the REIC/Dkk-3 fragments are expressed in PC3 cells. Adenovirus-LacZ and pDNR-CMV-GFP were used as negative controls and Adenovirus-REIC (full-length) was used as a positive control. The percentage of dead cells was determined 36 hours after infection when adenovirus was used and 72 hours after infection when plasmid was used. As shown in FIG. 2, fragments 1 and 2 were found to have high activity of inducing cell death. FIG. 3 shows the results of observation of cell conditions in such a case under a phase contrast microscope. Similarly, significantly lowered cell density was observed in fragments 1 and 2.

Example 2

Induction of Apoptosis by REIC/Dkk-3 Gene Fragment (2)

PC3 cells ($1 \times 10^5$ cells) were sowed in a 6-well plate, and pTracer-EF-A-1 (#1: 1-39 aa), -2 (#2: 1-78 aa), and -6 (Full: 1-350aa) plasmids into which cDNA of the REIC/Dkk-3 fragment had been inserted were introduced into PC3 cells using the TransIT®-Keratinocyte reagent (a transfection reagent, Mirus Bio Corporation) 24 hours later. Plasmids were introduced into OUMS-24 using the FuGENE®-HD reagent (a transfection reagent, Roche Applied Science). Forty eight hours thereafter, the cells remaining alive were subjected to nuclear staining with Hoechst 33342 and then observed under a fluorescent microscope. The percentage of the cells that had undergone apoptosis (i.e., cells in which nuclei were aggregated) was calculated using the GFP-positive cells (cells containing plasmids) as the denominator. Cell culture conditions employed in Example 1 were also employed.

Figure 4:
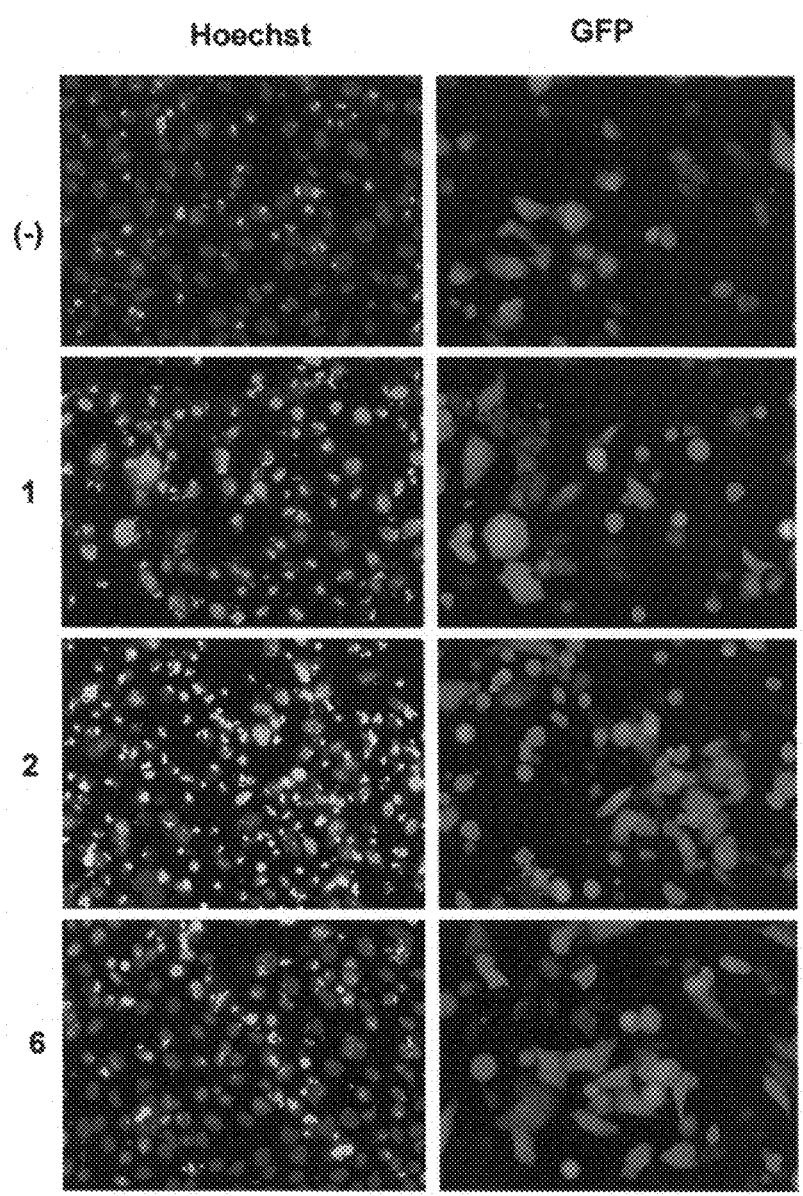
FIG. 4 is a photograph showing the conditions of PC3 cell death induced by the REIC/Dkk-3 gene fragments (part II).

Plasmids that had been used for gene introduction into PC3 are able to simultaneously express the inserted gene (i.e., the REIC/Dkk-3 fragment) and GFP with the use of separate promoters. Thus, detection of GFP (green) enables indirect detection of cells in which the REIC fragments are expressed. Induction of cell apoptosis was evaluated 48 hours after introduction. FIG. 4 shows a stained image. As shown in FIG. 4, GFP positive cells in which nuclei (stained with Hoechst: blue) have been significantly aggregated (i.e., apoptosis) were observed in the case of 1 and 2. In FIG. 4, the symbol (–) represents an empty plasmid, i.e., pTracer-EF-A, into which the REIC fragment has not been inserted.

Figure 5:
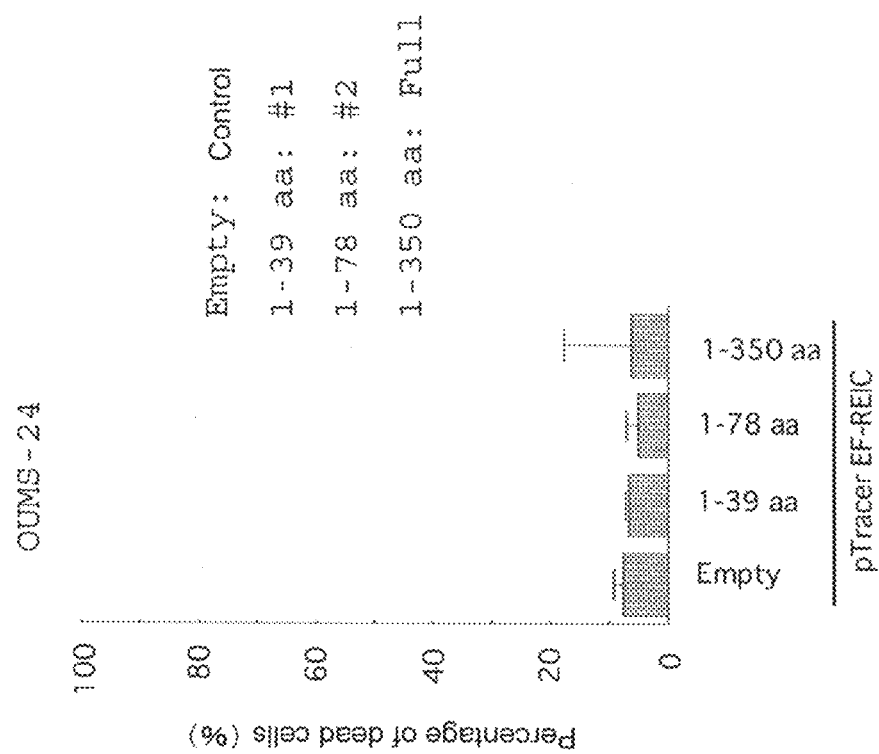
FIG. 5 shows the effects of PC3 and OUMS-24 for inducing apoptosis induced by the REIC/Dkk-3 gene fragments; wherein A shows the results regarding PC3 and B shows the results regarding OUMS-24.
Figure 5:
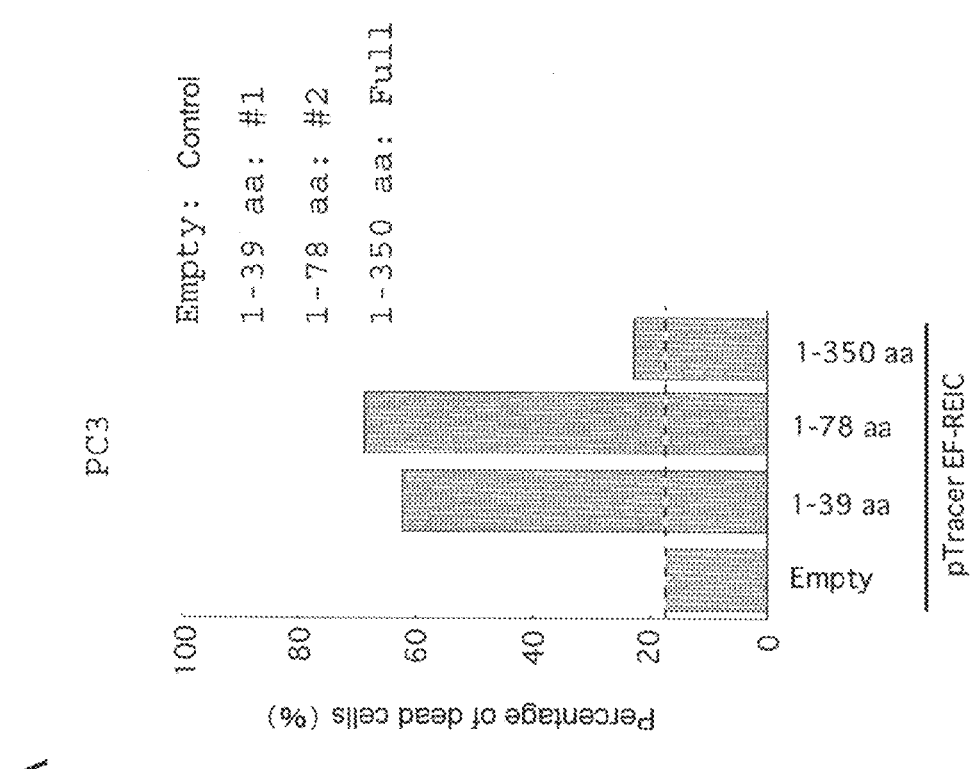

FIG. 5A shows the results of calculation of the percentage of apoptosis (i.e., cells in which nuclei were aggregated) with the use of PC3 by using the GFP-positive cells (cells containing plasmids) as the denominator. Significant effects of apoptosis induction were observed in the REIC fragments 1 (#1: 1-39 aa) and 2 (#2: 1-78 aa). FIG. 5B shows the results attained with the use of OUMS-24. The effects of apoptosis induction observed in PC3 were not observed in normal fibroblasts, OUMS-24.

Example 3

Induction of Endoplasmic Reticulum Stress Marker Protein by REIC/Dkk-3 Fragment

PC3 cells ($1\times10^7$ cells) were sowed in a 10-cm dish, and pTracer-EF-A-1 (#1: 1-39 aa), -2 (#2: 1-78 aa), and -6 (Full: 1-350aa) plasmids into which cDNA of the REIC fragment had been inserted were introduced into PC3 cells using the TransIT-Keratinocyte reagent (a transfection reagent) 24 hours later. Plasmids were introduced into OUMS-24 using the FuGENE-HD reagent (a transfection reagent). Forty eight hours thereafter, the cells were recovered and the sample was prepared via protein extraction. The resulting sample was subjected to SDS-PAGE, and expression analysis of the target protein was carried out via Western blotting.

Figure 6:
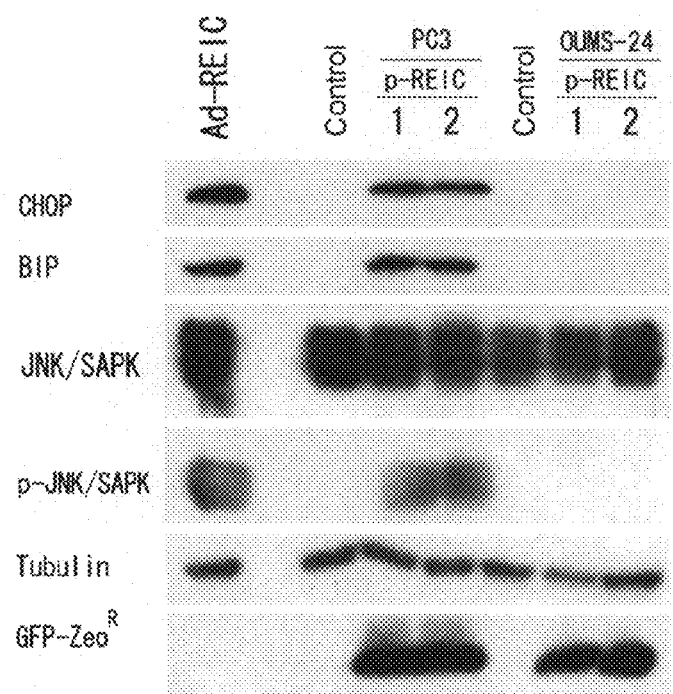
FIG. 6 is a photograph showing induction of the endoplasmic reticulum stress marker protein by the REIC/Dkk-3 fragment.

The results are shown in FIG. 6. In FIG. 6, "Ad-REIC" shows the results regarding the cells into which the adenovirus vector that induces overexpression of full-length REIC has been introduced. A "control" represents the results regarding the cells into which an empty plasmid (i.e., pTracer-EF-A) containing no REIC fragment has been inserted. In PC3 cells, both of 1(#1: 1-39 aa) and -2(#2: 1-78 aa) significantly induced phosphorylation of CHOP; BIP, and JNK, which were endoplasmic reticulum stress markers. Such phenomenon, however, was not observed in OUMS-24.

Example 4

Induction of Apoptosis in Mesothelial Tumor Cell Line by REIC/Dkk-3 Gene Fragment The 211H human malignant mesothelial tumor cells ($1\times10^5$ cells) were sowed in a 6-well plate, and pTracer-EF-A-1 (#1: 1-39 aa), -2 (#2: 1-78 aa), and -6 (Full: 1-350aa) plasmids into which cDNA of the REIC fragment had been inserted were introduced using the FuGENE®-HD (Roche Applied Science) and the CytoPure™ reagent (Nitto Denko Technical Corporation) 24 hours later. Forty eight hours thereafter, the cells remaining alive were subjected to nuclear staining with Hoechst 33342 and then observed under a fluorescent microscope. The percentage of the cells that had undergone apoptosis (i.e., cells in which nuclei were aggregated) was calculated using the GFP-positive cells (cells containing plasmids) as the denominator.

Figure 7:
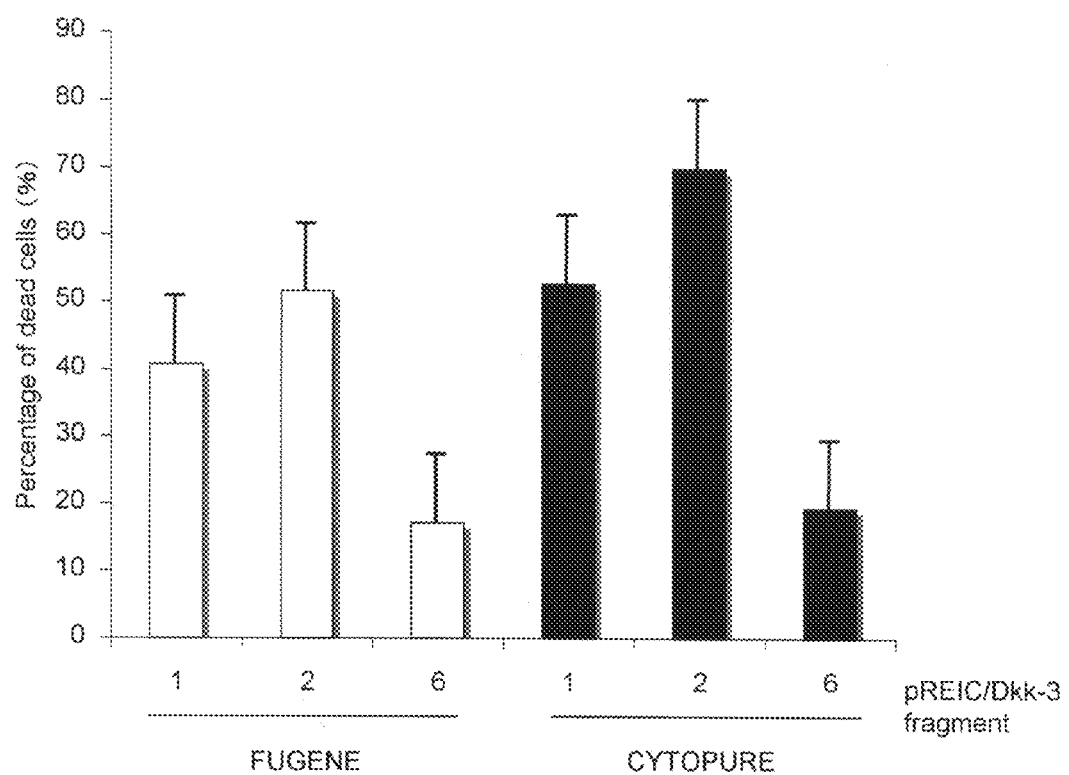
FIG. 7 shows induction of apoptosis in the mesothelial tumor cell line by the REIC/Dkk-3 gene fragment.
Figure 8:
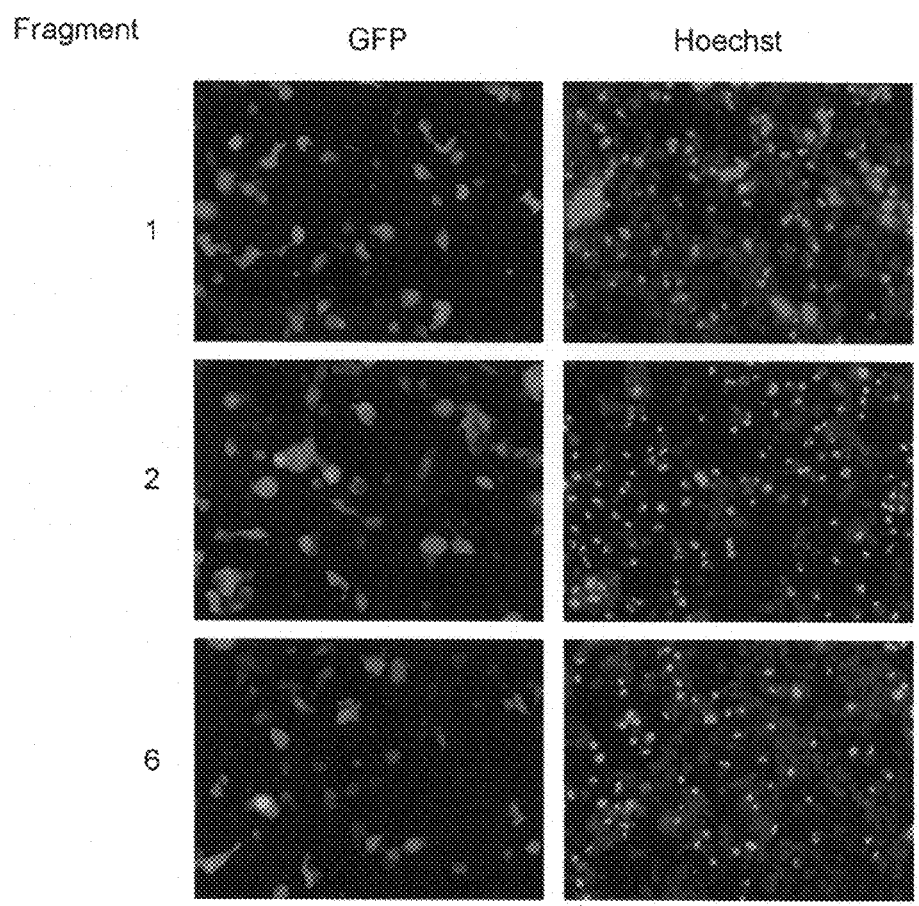
FIG. 8 is a photograph showing the conditions of cell death when a plasmid containing the REIC/Dkk-3 gene fragment as an induction reagent is introduced into the mesothelial tumor cell line using FuGENE.
Figure 9:
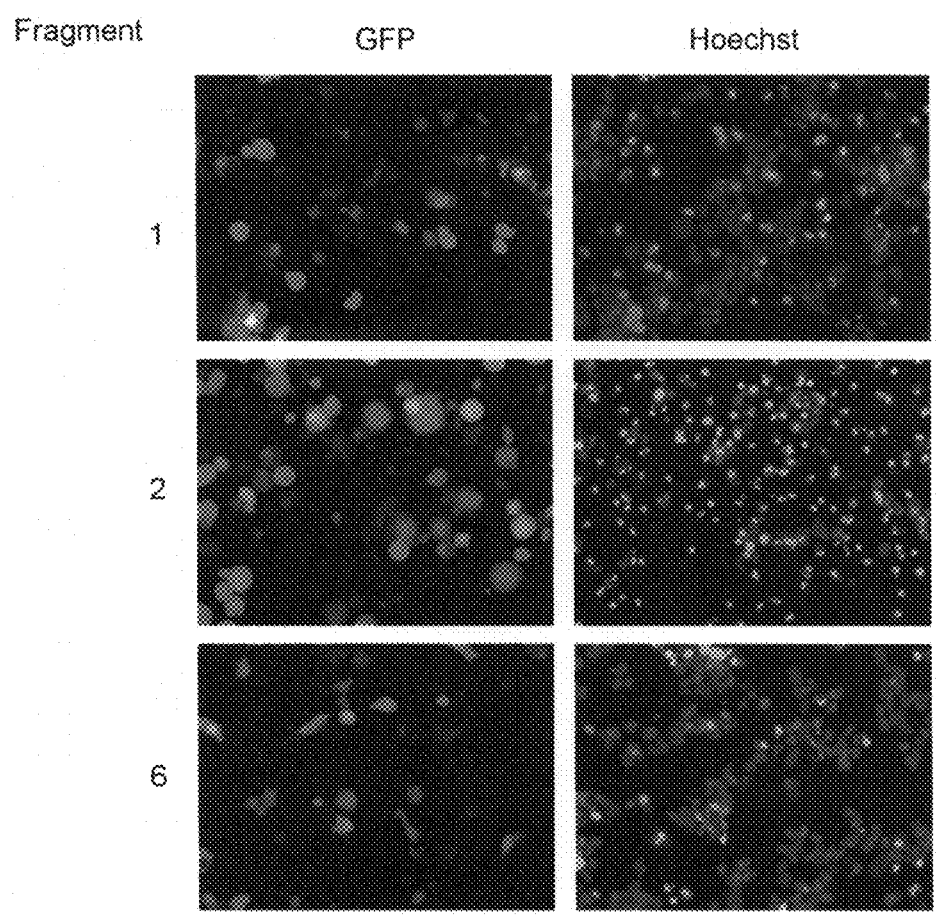
FIG. 9 is a photograph showing the conditions of cell death when a plasmid containing the REIC/Dkk-3 gene fragment as an induction reagent is introduced into the mesothelial tumor cell line using CytoPure.

The plasmids used for introduction are capable of simultaneous expression of an inserted gene (i.e., the REIC/Dkk-3 fragment) and GFP with the use of separate promoters. Thus, detection of GFP (green) enables indirect detection of cells in which the REIC fragments are expressed. Induction of cell apoptosis was observed under a fluorescent microscope and evaluated 48 hours after introduction. The percentage of the cells that had undergone apoptosis (i.e., cells in which nuclei were aggregated) was calculated using the GFP-positive cells (cells containing plasmids) as the denominator (FIG. 7). As a result, GFP positive cells in which nuclei (stained with Hoechst: blue) have been significantly aggregated (i.e., apoptosis) were observed as a result of the application of the FuGENE-HD reagent (FIG. 8) and the CytoPure reagent (FIG. 9) in the case of 1(1-39 aa) and 2(1-78 aa). The effects of apoptosis induction attained via application of the CytoPure reagent were slightly superior to those of a FuGENE-HD reagent (FIG. 7).

Example 5

Inhibition of Tumors In Vivo

Luciferase expression genes were incorporated into the human malignant mesothelial tumor cell line, 211H, to obtain the 211H clone 4 cells ($2\times10^6$ cells), the resultants were mixed with Matrigel, and the resultants were xenografted subcutaneously into nude mice. Conditions of subcutaneous tumor formation were inspected via IVIS (i.e., the high sensitivity in vivo luminescent imaging system) 3 days later, and a mixed solution of the pTracer-EF-A-2 (#2: 1-78 aa) plasmid/CytoPure was injected into the site of tumor formation (administration of 25 μg of plasmid once a day was continued for a week). Thereafter, administration was terminated, and the conditions of tumor formation were evaluated again via IVIS (i.e., the high sensitivity in vivo luminescent imaging system) 14 days thereafter. As control samples, the group subjected to single administration of Cytopure (CYTOPURE) and the group subjected to administration of Cytopure and a control vector (which expresses a red fluorescent protein, CYTOPURE+pDsRed) were provided.

Figure 10:
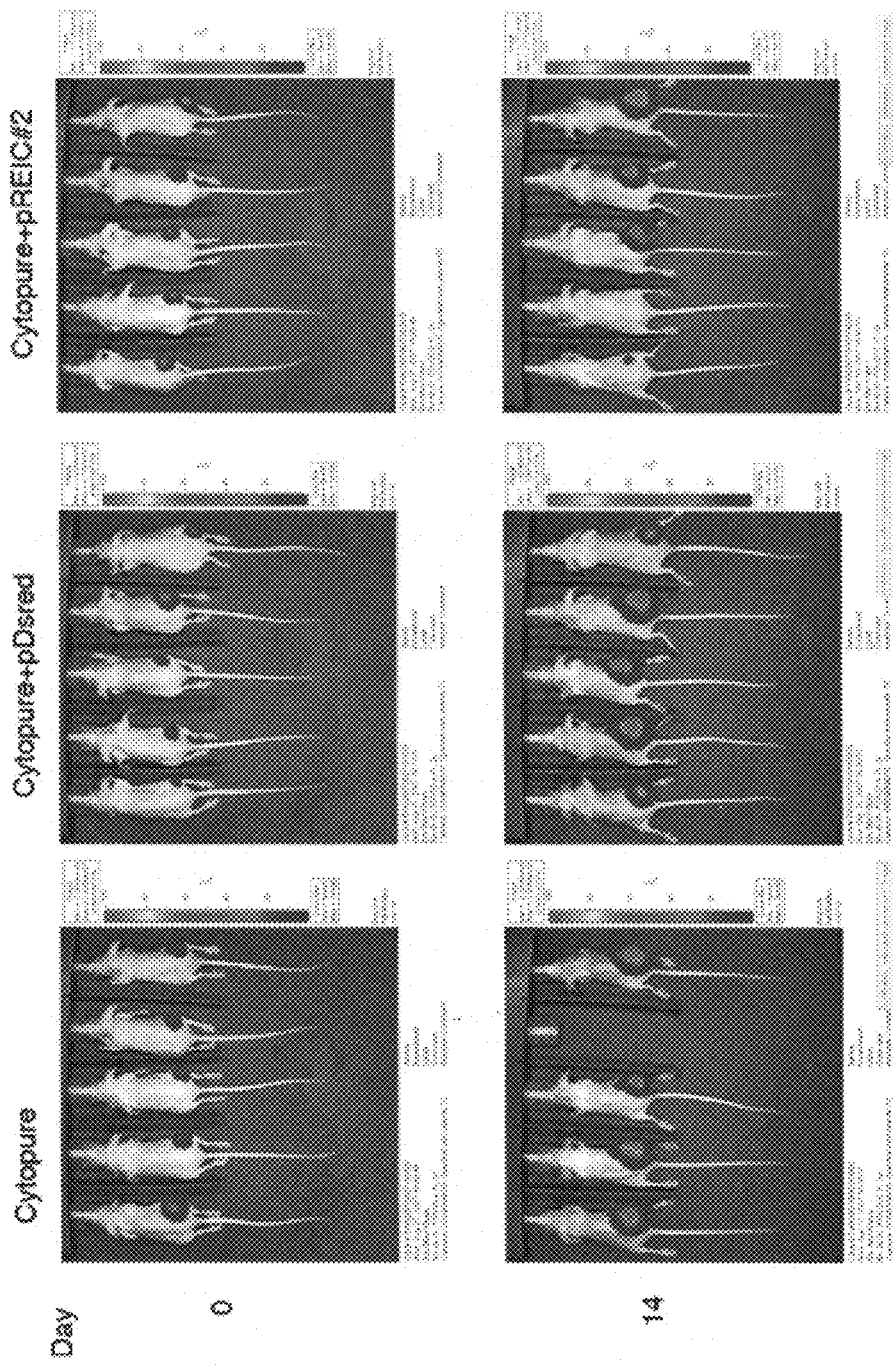
FIG. 10 is a photograph showing the effects of tumor suppression of the REIC/Dkk-3 gene fragment in vivo.

FIG. 10 shows the results. As shown in FIG. 10, tumors were substantially completely eliminated in 2 out of 5 mice to which the REIC fragments had been administered.

INDUSTRIAL APPLICABILITY

The REIC/Dkk-3 gene fragment of the present invention can be used as an inducer of apoptosis in cancer cells or a cancer therapeutic agent that can induce apoptosis in cancer cells, such as prostate cancer or mesoepithelioma, and can suppress such cancer. Also, the REIC/Dkk-3 gene fragment of the present invention and an expression product thereof have small molecular weights and thus are less likely to cause side effects.

All publications, patents, and patent applications cited herein are incorporated herein by reference in their entirety.

The invention claimed is:

1. A polynucleotide encoding a polypeptide fragment of the REIC/Dkk-3 protein, wherein the polypeptide fragment has apoptosis activity and the polynucleotide consists of a nucleotide sequence encoding any of the following polypeptides:

(i) a polypeptide consisting of SEQ ID NO: 4;
   (ii) a polypeptide consisting of SEQ ID NO: 6;
   (iii) a polypeptide consisting of amino acid 1 to any of amino acids 39 to 78 of the amino acid sequence of the REIC/Dkk-3 protein as shown in SEQ ID NO: 2, wherein the polynucleotide is a cDNA.

2. The polynucleotide according to claim 1, wherein said polynucleotide consists of a nucleotide sequence encoding the polypeptide consisting of SEQ ID NO: 4.

3. The polynucleotide according to claim 1, wherein said polynucleotide consists of the nucleotide sequence encoding the polypeptide consisting of SEQ ID NO: 6.

4. The polynucleotide according to claim 1, wherein said polynucleotide consists of a nucleotide sequence encoding a polypeptide consisting of amino acid 1 to any of amino acids 39 to 78 of the amino acid sequence of the REIC/Dkk-3 protein as shown in SEQ ID NO:2.

5. The polynucleotide according to claim 1, wherein said polynucleotide consists of SEQ ID NO:3.

6. The polynucleotide according to claim 1, wherein said polynucleotide consists of SEQ ID NO:5.

7. A cancer therapeutic agent comprising (a) a pharmacologically acceptable carrier, diluent or excipient; and (b) as an active ingredient, a polynucleotide according to claim 1 in (a).

* * * * *